(12) United States Patent
Marks

(10) Patent No.: US 7,816,410 B2
(45) Date of Patent: Oct. 19, 2010

(54) PESTICIDAL COMPOSITIONS

(75) Inventor: David Marks, Liverpool (GB)

(73) Assignee: Biofutures PI Ltd., Liverpool (GB)

( * ) Notice: Subject to any disclaimer, the term of this patent is extended or adjusted under 35 U.S.C. 154(b) by 1075 days.

(21) Appl. No.: 10/541,740

(22) PCT Filed: Dec. 2, 2004

(86) PCT No.: PCT/GB2004/005063
§ 371 (c)(1),
(2), (4) Date: Jun. 2, 2006

(87) PCT Pub. No.: WO2005/053395
PCT Pub. Date: Jun. 16, 2005

(65) Prior Publication Data
US 2007/0009616 A1   Jan. 11, 2007

(30) Foreign Application Priority Data
Dec. 2, 2003   (GB) ................................ 0327864.5

(51) Int. Cl.
A01N 65/08 (2009.01)
A01N 65/22 (2009.01)
A01N 65/06 (2009.01)
A61K 36/53 (2006.01)

(52) U.S. Cl. .................................................. 514/783

(58) Field of Classification Search .............. 514/783
See application file for complete search history.

(56) References Cited

U.S. PATENT DOCUMENTS

| | | | |
|---|---|---|---|
| 5,985,814 A * | 11/1999 | Zocchi et al. ............... 510/280 |
| 6,251,440 B1 | 6/2001 | Ryan et al. | |
| 6,444,458 B1 | 9/2002 | Singh et al. | |
| 6,548,085 B1 | 4/2003 | Zobitne et al. | |
| 6,849,614 B1 | 2/2005 | Bessette et al. | |
| 2001/0055628 A1 | 12/2001 | Hsu et al. | |
| 2002/0102281 A1 | 8/2002 | Auberger et al. | |
| 2002/0136789 A1 | 9/2002 | Singh et al. | |
| 2003/0064119 A1 | 4/2003 | Emerson | |
| 2003/0194454 A1* | 10/2003 | Bessette et al. ............. 424/745 |
| 2003/0203056 A1* | 10/2003 | Tumbers .................... 424/742 |
| 2005/0214337 A1 | 9/2005 | McGee et al. | |
| 2005/0260239 A1 | 11/2005 | Bencsits | |

FOREIGN PATENT DOCUMENTS

| | | |
|---|---|---|
| CH | 688787 A5 * | 3/1998 |
| EP | 0583774 A1 | 2/1994 |
| EP | 1036499 A1 | 9/2000 |
| WO | WO 00/64265 A2 | 11/2000 |
| WO | WO 01/91556 A2 | 12/2001 |
| WO | WO 01/91560 A3 | 12/2001 |
| WO | WO 03/001912 A1 | 1/2003 |
| WO | WO 03/033008 A1 | 4/2003 |
| WO | WO 2004/006679 A2 | 1/2004 |
| WO | WO 2005/058364 A2 | 6/2005 |

OTHER PUBLICATIONS

Ding, C., Wang, C.Y. 2003. The dual effects of methyl salicylate on ripening and expression of ethylene biosynthesis genes in tomato fruit. Plant Science. 164 (2003) 589-596.*
Angelini, Luciana G. et al.; "Essential Oils from Mediterranean Lamiaceae as Weed Germination Inhibitors"; 2003, *J. Agric. Food Chem.*, vol. 51, pp. 6158-6164.
Daferera, Dimitra J. et al.; "The effectiveness of plant essential oils on the growth of *Botrytis cinerea, Fusarium* sp. and *Clavibacter michiganensis* subsp. *michiganensis*"; 2003, *Crop Protection*, vol. 22, pp. 39-44.
Gil, A. et al.; "Essential oil yield and composition of *Tagetes minuta* accessions from Argentina"; 2000, *Biochemical Systematics and Ecology*, vol. 28, pp. 261-274.
Database Biosis Online: Biosciences Information Service, Database accession No. PREV199800083937 abstract, XP002323190, 1 page. Oct.-Nov. 1997.
Database Biosis Online: Biosciences Information Service, Database accesion No. PREV200300124420 abstract, XP002323191, 2 pages. Jan. 2003.
Database WPI: Section Ch, week 199918, Class C03, AN 1999-205420, abstract, XP002323192, 1 page. Dec. 16, 1998.

* cited by examiner

*Primary Examiner*—Johann R Richter
*Assistant Examiner*—Courtney Brown
(74) *Attorney, Agent, or Firm*—Townsend and Townsend and Crew LLP

(57) ABSTRACT

A pesticidal composition comprising (i) one or more essential oils selected from tagetes oil or a thymol containing oil such as thyme oil, or a mixture thereof, or components thereof which have insect repellent or deterrent properties, which have insect repellent or deterrent properties, wherein the total amount of such oil present does not exceed 10 % w/w; (ii) an agriculturally acceptable carrier oil and (iii) an emulsifier. In particular, the composition further comprises a compound, which remediates symptoms of viral infection, such as wintergreen oil. Use Of Compositions of this type in agriculture controls pests whilst reducing the amount of essential oil required. Furthermore, a combined effect of controlling insects, preventing reinfestation and viral symptom remediation is obtainable.

24 Claims, No Drawings

PESTICIDAL COMPOSITIONS

The present invention relates to pesticidal compositions, in particular to compositions that control insect or arachnid pests such as sucking insects, and their use, especially in agriculture. Certain compositions of the invention may also control the viruses that are vectored by these pests.

A number of natural oils, such as tagetes oil and thyme oil have been demonstrated to have insect repellent properties on several insect species. However, their potential for use in mainstream agriculture is limited due to two factors: economics and taint. Generally speaking, these oils, when applied alone to crops, have to be applied in amounts of from 2 to 5 liters of oil per hectare to achieve reasonable pest control. The use of the oils requires too much material to be used for them to be cost effective. Furthermore, when used in these quantities, the crops can suffer significant post harvest taint.

Essential oils have been used for the treatment of stored grain, but again, the amounts applied to achieve effective insect repellence is high.

The applicants have found however, that when formulated in a particular way, the amount of these oils needed to produce useful effects, can be significantly reduced.

According to the present invention there is provide a pesticidal composition comprising (i) one or more essential oils selected from tagetes oil or a thymol containing essential oil, or a mixture thereof, or components thereof which have insect repellent or deterrent properties, wherein the total amount of such oil or component present does not exceed 10& w/w; (ii) an agriculturally acceptable carrier oil and (iii) an emulsifier.

Thyme oil is a particularly suitable thymol containing essential oil, but others include *Anabasis, carum, lavendula, Ocimum*, and *ganum* oils.

In particular, the composition comprises one or more essential oils selected from tagetes oil or thyme oil, or a mixture thereof as element (i) above.

However, it is also possible that one or more isolated components of these oils may be utilised, provided these have insect repellent or deterrent properties.

For instance, *Thymus vulgaris* essential oil comprises a mixture of thymol, caracrol, cymol, linalool, terpin-4-ol an monoterpenoids. Any of these components or mixtures thereof may be used in the composition.

Components of tagetes oil such as *Tagetes erecta* and *Tagetes minuta* essential oil include dihydrotagetone, thiophenes and ocimene, or which dihydrotagetone is the most important component.

The agriculturally acceptable carrier oil acts as a carrier for the essential oil, allowing a smaller quantity of the essential oils to be evenly distributed on the crop, thus improving efficacy and reducing taint.

The composition suitably contains no more than 5% w/w of essential oil, more suitably no more than 3% w/w and preferably no more than 1.5% w/w of essential oil. For instance, the composition may contain no more than 1% w/w essential oil.

Using formulations of this type, effective pest control can be achieved by applying for instance from 1-5 liters per hectare and preferably about 2 liters per hectare of the composition to crops. This represents a significant reduction, for instance a reduction of between one and two orders of magnitude, of the amount of essential oil applied, as compared to the conventional methods of using these active ingredients.

They may also be applied in other environments, for example to stored grain, in order to reduce or eliminate pest damage. In this case, the amount of composition applied will be dependent on factors such as the nature of the grain and the level of the problem, but generally amounts of composition used will be such that the amount of essential oil is less than 0.01 ml/100 g grain, particularly less than 0.001 ml/100 g grain, and most particularly less than 0.0001 ml/100 g grain.

In order to achieve this, generally less than 10 ml/100 g grain, more suitably less than 1 ml/100 g grain, and preferably less than 0.1 ml/100 g grain of the composition are used.

The low concentrations of active components used in the compositions of the invention provides environmental benefits. In particular, adverse effects against beneficial insects such as bees, ladybirds (*Coccinella septempuncata*) and earthworms (*Eisenia foetida*) are minimised.

Particular examples of tagetes oil for use in the composition of the invention include the oil obtainable *Tagetes erecta*. Particular examples of thyme oil, for use in the compositions of the invention include the oil obtainable from *Thymus vulgaris*. The oils may be present alone or combinations of different oils may be included, provided the total essential oil content does not exceed the amounts specified above. Effective components of these oils are those which have insect repellent or deterrent properties.

Thus in a particular embodiment, the composition contains a mixture of tagetes oil and thyme oil, in ratios of from 3:1 to 1:3 and preferably about 1:1.

Such a composition shows particular synergistic effects in particular against whitefly.

In another embodiment, the composition comprises tagetes oil as component (i).

The agriculturally acceptable carrier oil is suitably a vegetable oil such as including canola oil (OSR), sunflower oil, cottonseed oil, palm oil and soybean oil.

The composition of the invention comprises an emulsifier, which may be any known agriculturally acceptable emulsifier. In particular, the emulsifier will comprise a surfactant, typically alkylaryl sulphonates, ethoxylated alcohols, polyalkoxylated butyl ethers, calcium alkyl benzene sulphonates, polyalkylene glycol ethers and butyl polyalkylene oxide block copolymers as are known in the art.

Nonyl phenol emulsifiers such as Triton N57™ are particular examples of emulsifiers, which may be used in the compositions of the invention, as are polyoxyethylene sorbitan esters such as polyoxyethylene sorbitan monolaurate (sold by ICI under the trade name "Tween™"). In some instances, natural organic emulsifiers may be preferred, particularly for organic farming applications. Coconut oils such as coconut diethanolamide is an example of such an compound. Palm oil products such as Lauryl stearate may also be used.

The emulsifier is suitably present in an amount which is sufficient to ensure that the composition has the desired miscibility with water. For instance, the emulsifier may be present in amounts of from 1 to 20% w/w, suitably up to 10% w/w and in particular about 6% w/w.

In a particular embodiment, the composition of the invention further comprises a compound which remediates symptoms of viral infection. Particular examples of such compounds may be compounds which reduce ethylene production or have antiviral effects.

Ethylene production is increased following infection with many viruses, and application of compounds, which reduce this, can be used to remediate symptoms.

A particular example of compounds which are known to reduce ethylene production are salicylate compounds such as salicyclic acid or esters thereof, in particular alkyl ester. Examples of alkyl esters include $C_{1-10}$ alkyl esters such as methyl salicylate.

Suitably, the salicylate compound used in the composition is in the form of an essential oil. Examples of essential oils which include salicylic acid or salicylates include wintergreen oil, as well as oils from Chenopodium, Erythroxylum, Eugenia, Gaultheria, Myristica, Syzygium, Xanthophyllum, Cinnamonium, Gualtheria, Gossypium and mentha.

For example, wintergreen oil contains a high proportion of methyl salicylate, and therefore forms a readily useable source of active ingredient, which is readily miscible with the composition.

Plants respond to compound as it volatilises, so a thorough even coverage is essential to the efficacy of this compound if it is to be effective under field conditions. Incorporation into an oil-based formulation of the invention ensures that this occurs.

Alternatively or additionally, the compound used may be used compounds which have antiviral activity and such as jasmonic acid or derivatives thereof. Particular derivatives are alkyl esters such as $C_{1-10}$alkyl esters such as methyl jasmonate.

The composition of the invention need only contain a relatively small amount of such a compound, for example up to 0.1% w/w, and preferably only a trace amount up to 0.005% w/w for instance, 0.001% w/w. Where this is administered in the form of an essential oil, the amount of oil added should be sufficient to ensure that the desired concentration of the active compound is supplied. In this context, oils with relatively high concentrations of the compounds, such as wintergreen oil, may be preferred.

The inclusion of such components, and in particular wintergreen oil, has been found to produce synergistic insecticidal effects against mites, in particular when used in combination with tagetes oil.

Thus a particularly preferred composition comprises a combination of tagetes oil and wintergreen oil, wherein the tagetes oil forms at least part of component (i) of the composition, and the wintergreen oil is component (iv) as described above.

When used against whitefly, synergism between the individual components (i.e. between tagetes and the thymol containing essential oil as discussed above, but also between a thymol containing essential oil and wintergreen oil and tagetes and wintergreen oil), has also been noted.

Thus in a particular embodiment, the composition contains a mixture of tagetes oil and a thymol containing essential oil such as thyme oil, in ratios of from 3:1 to 1:1.

In an alternative embodiment, the composition contains a mixture of a thymol containing essential oil such as thyme oil and wintergreen oil, wherein the a thymol containing essential oil such as thyme oil forms at least part of component (i) of the composition, and the wintergreen oil is component (iv) as described above.

Mixtures comprising tagetes oil and a thymol containing essential oil such as thyme oil as component (i) and wintergreen oil as component (iv) are particularly preferred as they provide effective protection against both whitefly and mites.

In this particular embodiment, the composition can be used as a "one product strategy" for dealing with several separate but related issues. Specifically it can tackle aphids and other sucking insects and the virus that they vector by:

a) Destroying insects already present;

b) Deterring reinfestation; and c) Helping the plant recover from virus

Insects already present on treated crops when the composition of the invention is applied are killed by the agriculturally acceptable carrier oil such as the vegetable oil. This acts by suffocation of the insects and has ovicidal properties, and so reduces the sources for reinfestation.

The presence of the insect repellent or deterrent discourages reinfestation. Furthermore, by including a compound such as methyl salicyclate, the composition will remediate any virus which has been vectored by the insects.

The combined approach yields better results than using separate materials.

Thus in a further aspect, the invention provides a pesticidal composition comprising (i) one or more essential oils selected from tagetes oil or a thymol containing essential oil, or a mixture thereof, or components thereof which have insect repellent or deterrent properties; (ii) an agriculturally acceptable carrier oil; (iii) an emulsifier; and (iv) a compound which remediates symptoms of viral infection.

Particularly suitable components (i)-(iv) and preferred relative amounts used are as set out above.

Compositions are suitably prepared by mixing the components together in a conventional manner. Suitably, the essential oil(s), the viral symptom remediation component and the emulsifier are added to the agriculturally acceptable carrier oil and mixed with stirring until the components are evenly diluted throughout the composition.

The compositions of the invention are suitably diluted in water before application. Thus the compositions described above are generally concentrates.

Thus in a further aspect, the inventions provide a formulation for administration to insect pests or to the environment of the insect pests, the formulation comprising a composition as described above, and water.

The amount of water used will depend upon the particular mode of administration of the pesticidal formulation, and to where it is being applied, for example to crops or to grain stores of the like. This will generally be by means of a sprayer, such as an electrostatic or other conventional sprayer. In general, the final formulation will contain from 10-20% of the composition of the invention and the remainder is water.

In yet a further aspect, the invention provides a method for killing or controlling insect pests which method comprises applying to the pests or to the locus thereof, a composition as described above.

Suitably, the composition is one that contains a component, which remediates viral infection, and so the treatment provides a combined pesticidal and viral symptom remediation effect.

The compositions and methods of the invention can be used to treat a variety of crops affected by various insects and arachnids, including aphids, thrips, leafhoppers, greenfly, whitefly, and mites. Whitefly species which may be controlled include *Trialeurodes vaporariorum* (Glass House Whitefly), *Trialeurodes abutilonea, Aleurothirus floccosus, Aleurodicus disperses, Bemisia argentifolia* (Silverleaf whitefly), *Bemisia tabaci, Bemesia graminus, Pseudaulacaspis pentagona* (white peach scale), and in particular *Trialeurodes vaporariorum* (Glass House Whitefly), *Bemisia argentifolia* (Silverleaf whitefly) and *Pseudaulacaspis pentagona* (white peach scale).

Thrips species which may be controlled include *Thrips tabaci, Scitothrips aurantii, Scirtothrips citri, Limnothrips cerealium, Haplothrips tritici, Kanothrips robustus, Diarthrothrips coffeae, Taeniothrips inconsequeus, Taeniothrips simplex, Heterothrips azaleae, Liothrips oleae, Caliothrips* sp., *Frankiniella* sp., *Heliothrips haemorhoidalis* and *Thrips palmi*, and in particular *Frankiniella* sp.

Important aphid pests which may be controlled include *Aphis fabae* (Black Bean aphid), *Acyrthosiphum pisum* (pea aphid), *Brevicoryne brassicae* (cabbage aphid), *Sitobion avenae* (grain aphid), *Cavariella aegopodii* (carrot aphid), *Aphis craccivora* (groundnut aphid), *Aphis gossypii, Aphis nasturii,*

*Aphis citricol, Aphis craccivora, Toxoptera aurantii* (black citrus aphid), *Cavariella* spp., *Chaitopherus* spp., *Cinara* spp., *Drepanoiphum platanoides, Elatobium* spp., *Myzus ascalonicas, Myzus persicae, Myzus ornatus, Rhopalosihum padi, Sitobion avenae* and *Metopolophium dirhodum*. Particular examples are *Aphis gossypii* and *Myzus persicae*.

Mites which may controlled include *Panonychus* sp. such as *Panonychus citri* (citrus red mite), and *Panonychus ulmi* (red spider mite), *Tetranychus* sp. such as *Tetranychus kanzawi* (Kanzawa spider mite), *Tetranychus urticae* (2 spotted spider mite), *Tetranychus pacificus* (Pacific spider mite), *Tetranychus turkestanii* (Strawberry mite) and *Tetranychus cinnabarinus* (Carmine spider mite), *Oligonychus* sp. such as *Oligonychus panicae* (avacado brown mite), *Oligonychus perseae* (persea mite), *Oligonychus pratensis* (Banks grass mite) and *Oligonychus coffeae, Aculus* sp. such as *Aculus cornatus* (Peach silver mite), *Aculus fockeni* (plum rust mite) and *Aculus lycopersici* (tomato russet mite), *Eotetranychus* sp. such as *Eotetranychus wilametti, Eotetranychus yumensis* (yuma spider mite) and *Eotetranychus sexmaculatis* (6-spotted mite), *Bryobia rubrioculus* (brown mite), *Epitrimerus pyri* (pear rust mite), *Phytoptus pyri* (Pear leaf blister mite), *Acalitis essigi* (red berry mite), *Polyphagotarsonemus latus* (Broad mite), *Eriophyes sheldoni* (citrus bud mite), *Brevipalpus lewisi* (citrus flat mite), *Phylocoptruta oleivora* (citrus rust mite), *Petrobia lateens* (Brown wheat mite), *Oxyenus maxwelli* (olive mite), *Rhizoglyphus* spp., *Tyrophagus* spp., *Diptacus gigantorhyncus* (bigheaded plum mite) and *Penthaleaa major* (winter grain mite)

Specific mite species which are well controlled using the invention include *Panonychus* sp. such as *Panonychus citri* (citrus red mite), and *Panonychus ulmi* (red spider mite), *Tetranychus* sp. such as *Tetranychus kanzawi* (Kanzawa spider mite), and *Tetranychus urticae* (2 spotted spider mite), and *Phylocoptruta oleivora* (citrus rust mite).

In particular, the compositions of the invention are particularly effective at controlling whitefly, and mites such as *Tetranychus urticae, Panonychus ulmi* (fruit tree spider mite) ort *Panonychus citri* (citrus red mite). They have been found to show an extremely good repellent effect against adult pests, but also provided control of nymphs, and a good ovicidal effect, in particular against mite eggs.

This is very useful as none of the currently available methods show a particularly good effect against mite eggs.

The product is suitable for use on most crops, but in particular can be used for the treatment of greenhouse crops, vegetables, and fruit crops.

The compositions have low phytotoxicity at the effective concentrations. They appear to act as contact insecticides, and are not well translocated through plant tissue. However, they do persist well when applied to plant tissue, and so provide reasonable protection over a period of time.

The invention further provides the use of a composition as described above which contain a compound which remediates viral symptoms, as a combined pesticidal/viral symptom remediation composition.

Alternatively, the invention provides the use of a composition or a formulation as described above, as an adjuvant for an insecticide or acaricide.

In a particular embodiment, the invention provides the use of a composition as described above as an insecticide or acaricide, for administration to crops at a rate of less than 5 liters per hectare, and preferably at no more than 2 liters per hectare.

The amount of composition applied in any particular situation will vary depending upon a number of factors such as the nature of the crop, the level of pest infestation etc. Typically however, for use on crops, from 2-5 liters of the composition of the invention before water is added, will be applied per hectare. Thus the amount of essential oil added will generally be from 0.02 to 0.5 liters per hectare. This is significantly lower than conventional methods.

The compositions can be used either alone (and in this case, they may be suitable for organic growers) or in conjunction with other insecticides or acaricides. In the latter case, the composition of the invention can lead to an improvement in performance of the other insecticide or acaricide, and thus it produces an adjuvant effect. It may further reduce application rate and frequency, remediate virus symptom infection and leave a deterrent.

The invention will now be particularly described by way of example.

EXAMPLE 1

Composition

The following components were mixed together in the amounts listed:

| Component | % w/w of total |
|---|---|
| Soybean Oil | 93.50 |
| Tagetes oil | 00.50 |
| Thymus oil | 00.50 |
| Wintergreen oil | 00.001 |
| Triton N57 ™ | 6.00 |

The resultant composition (Composition A) can be applied to crops, where it kills pests. The residual deterrent or repellent on the crops reduces the incidence of reinfestation. Furthermore, symptoms of any viral infection, caused by the insect vectors, are remediated.

EXAMPLE 2

Control of Whitefly

The aim of this study was to determine the efficacy of the compositions of the invention on separate life stages of the glasshouse whitefly (*Trialeurodes vaporariorum*).

Three studies were undertaken, the first to determine the efficacy of the composition of the invention as an ovicide in both protectant and curative treatments. The following composition (Composition B) was prepared:

| Component | % w/w of total |
|---|---|
| Tagetes oil | 00.60 |
| Thymus oil | 00.60 |
| Wintergreen oil | 00.001 |
| Polyoxyethylene sorbitan monolaurate | 4.90 |
| Canola Oil | Balance |

A second test was to determine the efficacy of composition B as a curative treatment against whitefly nymphs and the third test was to determine the effects of the composition as a (repellent) protectant spray against whitefly adults.

All treatments were applied to tobacco plants (var. Tobacco nicotiana) using a hand-held atomiser (CEME-984), applied to both surfaces of the leaf, to incipient run-off. The composition was applied at 5000, 1000, 200, 100 and 50 mL product/ hL, Imidacloprid (reference item) was applied at 15 gai/hL and controls were sprayed with deionised water only.

Three replicate plants were sprayed for each treatment. The treated plants were maintained in a controlled environment room at 22.9-34.4° C., with lighting on a 16 h light/8 h dark cycle. Light intensity was recorded as 870-1464 lux. Relative humidity was recorded as being between 25.1-85.2%.

For the ovicide test, plants were treated (both infested and uninfested with eggs). For the curative test, leaf discs were taken and egg numbers counted. For the protectant test, treated plants were infested after treatment then leaf discs taken with known numbers of eggs. Assessments of egg hatch were made at 3, 6 and 7 days after treatment (DAA) for both curative and protectant tests.

For the curative nymph test, leaves with nymphs 7-12 days old were treated and assessments of mortality made at 4, 7 and 10 days after application.

The adult protectant test, assessed the numbers of alive adults on treated leaves after immersion in an adult whitefly infested chamber, 15 and 18 days after application.

No phytotoxicity was seen with composition B at rates up to and including 5000 mL product/hL on tobacco leaves.

The results of the assessments are summarised in the tables in Tables 1-4 below.

TABLE 1

RESULTS FOR OVICIDE PROTECTANT TEST (Showing percentage whitefly egg hatch - mean of three replicates).

| Treatment | Assessment time-days after application (DAA) | | |
|---|---|---|---|
| | 1 | 3 | 7 |
| Control (water only) | 0.0 | 0.0 | 100.0 |
| Composition B @ 50 mL/hL | 0.0 | 0.0 | 100.0 |
| Composition B @ 100 mL/hL | 0.0 | 0.0 | 100.0 |
| Composition B @ 200 mL/hL | 0.0 | 0.0 | 100.0 |
| Composition B @ 1000 mL/hL | 0.0 | 0.0 | 0* |
| Composition B @ 5000 mL/hL | 0.0 | 0.0 | 36.4** |
| Imidacloprid @ 15 gai/hL | 0.0 | 0.0 | 0.0 |

*No eggs laid
**low numbers of eggs laid

These results show that composition B reduced egg hatch at the 5000 and 1000 mL product/hL rates although few eggs were laid on treated leaves at these rates.

TABLE 2

RESULTS FOR OVICIDE CURATIVE TEST (showing percentage whitefly egg hatch - mean of three replicates).

| Treatment | Assessment time-days after application (DAA) | | |
|---|---|---|---|
| | 1 | 3 | 7 |
| Control (water only) | 0.0 | 95.5 | 100.0 |
| Composition B @ 50 mL/hL | 0.0 | 90.4 | 100.0 |
| Composition B @ 100 mL/hL | 0.0 | 98.7 | 100.0 |
| Composition B @ 200 mL/hL | 0.0 | 97.6 | 100.0 |
| Composition B @ 1000 mL/hL | 0.0 | 100.0 | 100.0 |
| Composition B @ 5000 mL/hL | 0.0 | 98.7 | 99.2 |
| Imidacloprid @ 15 gai/hL | 0.0 | 75.2 | 91.4 |

Only a very slight reduction in egg hatch was seen with the composition of Example 1 at the 5000 mL/hL rate and imidacloprid (99.2 and 91.4%) respectively compared to 100% hatch at all other rates tested.

TABLE 3

RESULTS FOR NYMPH CURATIVE TEST (showing percentage whitefly nymph mortality - mean of three replicates).

| Treatment | Assessment time-days after application (DAA) | | |
|---|---|---|---|
| | 4 | 7 | 10 |
| Control (water only) | 0.0 | 0.0 | 0.0 |
| Composition B @ 50 mL/hL | 0.0 | 0.0 | 0.0 |
| Composition B @ 100 mL/hL | 0.0 | 81.5 | 81.5 |
| Composition B @ 200 mL/hL | 0.0 | 72.6 | 72.6 |
| Composition B @ 1000 mL/hL | 0.0 | 88.6 | 88.6 |
| Composition B @ 5000 mL/hL | 84.6 | 98.7 | 98.7 |
| Imidacloprid @ 15 gai/hL | 100.0 | 100.0 | 100.0 |

The composition B gave good control of whitefly nymphs from 100 to 5000 mL/hL.

TABLE 4

RESULTS FOR ADULT REPELLENCE TEST (number of adult whitefly per leaf (mean of three replicates).

| Treatment | Assessment time-days after application (DAA) | |
|---|---|---|
| | 15 | 18 |
| Control (water only) | 37 | 144 |
| Composition B @ 50 mL/hL | 50 | 143 |
| Composition B @ 100 mL/hL | 42 | 195 |
| Composition B @ 200 mL/hL | 70 | 132 |
| Composition B @ 1000 mL/hL | 1 | 3 |
| Composition B @ 5000 mL/hL | 2 | 2 |
| Imidacloprid @ 15 gai/hL | 0 | 0 |

Low numbers of adults on leaves treated with the composition B at rates of 5000 and 1000 mL/hL.

CONCLUSIONS

These results show that Composition B gave excellent preventative egg control (similar to imidacloprid @ 15 gai/hL) when applied as a preventative spray at rates of 1000 and 5000 mL/hL.

Furthermore, this composition at rates of 100 to 5000 mL/hL gave excellent control of nymphs and repelled adults from treated leaves at rates of 1000 and 5000 mL product/hL.

EXAMPLE 3

Control of Mites

The aim of this study was to determine the efficacy of the compositions of the invention against the red spider mite *Tetranychus urticae*. The composition of Example 2 was assessed at application rates of 5000, 1000, 200, 100, and 50 mL composition/hL, along with a deionised water only control and a reference item (Dynamec, comprising Abamectin at 18 g/L (1.88% w/w)) sprayed at 50 mL product/hL.

All treatments were applied to the top (dorsal) surface of dwarf French bean leaf discs (var. The Prince) using a Potter Tower sprayer delivering a spray volume of 393.8 L/ha. Three leaf discs were sprayed for each treatment.

At each of the assessment times, leaf discs were cut and placed, treated surface uppermost, in petri dishes containing water-saturated cotton wool. The discs were infested with either mite adults, nymphs or eggs. The leaf discs were either taken from infested cultures for the curative test or infested by transferring eggs, nymphs or adults using a fine paint brush.

The infested leaf discs were maintained in a controlled environment room at 22.4-26.9° C. and 38.4-87.1% relative humidity. The lighting regime was 16 hours light/8 hours dark with a light intensity of 250-383 lux.

Assessments of mortality were carried out at times one, three and seven days after application. Mortality assessments of the nymphs and adults were only made at one and three DAA because of natural mortality.

For the test to be considered valid, mortality in the controls at each time point assessment should not have exceeded 20% (actual total mortality ranged from 0 to 13.3%). No phytotoxicity was seen with Example 1 at rates up to and including 5000 mL product/hL on French bean.

The results of the assessments for mortality are summarised in the tables 5-10 below.

TABLE 5

RESULTS FOR OVICIDE PROTECTANT TEST
Percentage mite egg hatch (mean of three replicates).

| Treatment | Assessment time days after application (DAA) | | |
|---|---|---|---|
| | 1 | 3 | 7 |
| Control (water only) | 16.7 | 50.0 | 100.0 |
| Composition B @ 50 mL/hL | 10.0 | 63.3 | 100.0 |
| Composition B @ 100 mL/hL | 20.0 | 70.0 | 100.0 |
| Composition B @ 200 mL/hL | 7.9 | 18.4 | 94.7 |
| Composition B @ 1000 mL/hL | 9.7 | 45.2 | 45.2 |
| Composition B @ 5000 mL/hL | 6.5 | 32.3 | 32.3 |
| Dynamec @ 50 g/hL | 9.7 | 32.3 | 100.0 |

Composition B reduced egg hatch from rates of 200 mL product/hL at seven DAA. Dynamec, a leading mite treatment produced no egg mortality at 50 mL/hL seven DAA.

TABLE 6

RESULTS FOR NYMPH PROTECTANT TEST
Percentage mite nymph mortality (mean of three replicates).

| Treatment | Assessment time days after application (DAA) | |
|---|---|---|
| | 1 | 3 |
| Control (water only) | 2.9 | 2.9 |
| Example 1 @ 50 mL/hL | 0.0 | 42.3 |
| Composition B @ 100 mL/hL | 13.0 | 17.4 |
| Composition B @ 200 mL/hL | 34.5 | 51.7 |
| Composition B @ 1000 mL/hL | 85.7 | 89.3 |
| Composition B @ 5000 mL/hL | 96.7 | 100.0 |
| Dynamec @ 50 g/hL | 100.0 | 100.0 |

In this case, Dynamec produced 100% control at 50 mL product/hL 3 DAA. However, the formulation of Example 2 produced similar control to Dynamec at 5000 mL/hL.

TABLE 7

RESULTS FOR ADULT PROTECTANT TEST
Percentage mite adult mortality (mean of three replicates).

| Treatment | Assessment time days after application (DAA) | |
|---|---|---|
| | 1 | 3 |
| Control (water only) | 0.0 | 13.3 |
| Composition B @ 50 mL/hL | 3.3 | 30.0 |

TABLE 7-continued

RESULTS FOR ADULT PROTECTANT TEST
Percentage mite adult mortality (mean of three replicates).

| Treatment | Assessment time days after application (DAA) | |
|---|---|---|
| | 1 | 3 |
| Composition B @ 100 mL/hL | 6.7 | 30.0 |
| Composition B @ 200 mL/hL | 16.7 | 23.3 |
| Composition B @ 1000 mL/hL | 80.0 | 100.0 |
| Composition B @ 5000 mL/hL | 96.7 | 100.0 |
| Dynamec @ 50 g/hL | 100.0 | 100.0 |

In this test, the formulation of Example 2 at 5000 and 1000 mL/hL produced a similar control to Dynamec at 50 mL/hL 3 DAA.

TABLE 8

RESULTS FOR OVICIDE CURATIVE TEST
Percentage mite egg hatch (mean of three replicates).

| Treatment | Assessment time days after application (DAA) | | |
|---|---|---|---|
| | 1 | 3 | 7 |
| Control (water only) | 5.1 | 56.0 | 100.0 |
| Composition B @ 50 mL/hL | 3.8 | 69.9 | 100.0 |
| Composition B @ 100 mL/hL | 7.4 | 68.7 | 100.0 |
| Composition B @ 200 mL/hL | 0.0 | 28.1 | 100.0 |
| Composition B @ 1000 mL/hL | 1.2 | 13.0 | 10.9 |
| Composition B @ 5000 mL/hL | 0.0 | 2.5 | 10.5 |
| Dynamec @ 50 g/hL | 0.0 | 3.0 | 39.1 |

The composition of Example 2 is clearly a better ovicide than Dynamec at rates of 1000 and 5000 mL/hL.

TABLE 9

RESULTS FOR NYMPH CURATIVE TEST
Percentage mite nymph mortality (mean of three replicates).

| Treatment | Assessment time days after application (DAA) | |
|---|---|---|
| | 1 | 3 |
| Control (water only) | 0.0 | 0.0 |
| Composition B @ 50 mL/hL | 13.1 | 55.1 |
| Composition B @ 100 mL/hL | 8.3 | 34.5 |
| Composition B @ 200 mL/hL | 9.6 | 36.2 |
| Composition B @ 1000 mL/hL | 77.6 | 89.5 |
| Composition B @ 5000 mL/hL | 94.2 | 100.0 |
| Dynamec @ 50 g/hL | 100.0 | 100.0 |

The composition of Example 2 provided similar control to Dynamec at 5000 mL/hL with 55% mortality at 50 mL/hL.

TABLE 10

RESULTS FOR ADULT CURATIVE TEST
Percentage mite adult mortality (mean of three replicates).

| Treatment | Assessment time days after application (DAA) | |
|---|---|---|
| | 1 | 3 |
| Control (water only) | 0.0 | 2.4 |
| Composition B @ 50 mL/hL | 10.7 | 17.9 |
| Composition B @ 100 mL/hL | 3.1 | 21.9 |
| Composition B @ 200 mL/hL | 13.6 | 36.4 |

TABLE 10-continued

RESULTS FOR ADULT CURATIVE TEST
Percentage mite adult mortality (mean of three replicates).

| Treatment | Assessment time days after application (DAA) | |
|---|---|---|
| | 1 | 3 |
| Composition B @ 1000 mL/hL | 57.1 | 92.9 |
| Composition B @ 5000 mL/hL | 88.9 | 100.0 |
| Dynamec @ 50 g/hL | 100.0 | 100.0 |

The composition of Example 2 shows similar control to Dynamec at 5000 mL/hL with 18% mortality at 50 mL/hL (3 DAA).

These results show that the composition of Example 2 had superior mite egg control than Dynamec when applied as a curative spray at rates of 1000 and 5000 mL/hL. In the protectant test seven days after application and infestation, only the composition of Example 1 at rates of 200, 1000, and 5000 mLs product/hL reduced egg hatch (94.7, 45.2 and 32.3% egg hatch respectively). Dynamec had no effect on egg hatch at 50 mL product/hL.

The composition of Example 2 at rates of 1000 and 5000 mL/hL also had excellent control of both nymphs and adults in both curative and protectant sprays.

EXAMPLE 4

Synergistic Effects Against Mites

The aim of this study was to determine if synergism exists between the three active components of the composition of the invention and to find the best optimisation for the active components.

Three separate formulations each containing a single active constituent of Composition B in Example 2 namely Tagetes, Thymus and Wintergreen oils were prepared as follows:

| Composition C | |
|---|---|
| Component | % w/w of total |
| Tagetes oil | 00.75 |
| Polyoxyethylene sorbitan monolaurate | 4.90 |
| Canola Oil | Balance |

| Composition D | |
|---|---|
| Component | % w/w of total |
| Thymus oil | 00.75 |
| Polyoxyethylene sorbitan monolaurate | 4.90 |
| Canola Oil | Balance |

| Composition E | |
|---|---|
| Component | % w/w of total |
| Wintergreen oil | 00.001 |
| Polyoxyethylene sorbitan monolaurate | 4.90 |
| Canola Oil | Balance |

These were then tested alone and in combination (ratios of 1:1, 1:3 and 3:1) to assess their efficacy against motile stages of *Tetranychus urticae*. Composition B was also tested at the same time.

Two studies were undertaken. In the first, the samples were tested alone at the following rates—2000, 1000, 500, 250 and 125 mL product/hL, along with a water only control to determine the relative activity of the samples and the optimum rates to be tested in the second study.

In the second study, the samples were again tested alone at the following rates—3000, 1000, 333, 111 and 37 mL product/hL. Combinations of the formulations of 1:1, 3:1 and 1:3 were also tested at rates of 3000, 1000, 333, 111 and 37 mL product/hL to determine their relative EC50 values.

All treatments were applied to French bean leaf discs (previously infested with *T. urticae*) using a Potter Tower sprayer. Leaf discs were sprayed at an application rate of 400l/ha to ensure adequate coverage. Three replicate discs were sprayed for each treatment. At each of the assessment times, (pre-treatment, one and three days after application (DAA)) the leaf discs were examined under a binocular microscope for living motile mites.

Mean mite mortality and percent mortality was calculated. EC50 values were also calculated using ToxCalc V5.0 using the statistical model with the best fit to the data.

The results of the assessments for mite mortality and EC50 values are summarised in the tables 11 and 12 below.

TABLE 11

Percent mortality values for formulations v *T. urticae*.

| Trt rate(mL product/hL) | Composition B | Composition C | Composition E | Composition D |
|---|---|---|---|---|
| 2000 | 96.30 | 98.2 | 100 | 98.37 |
| 1000 | 92.42 | 95.23 | 100 | 94.87 |
| 500 | 91.67 | 89.56 | 89.49 | 62.09 |
| 250 | 86.97 | 71.24 | 53.47 | 26.83 |
| 125 | 59.92 | 63.86 | 27.03 | 36.6 |
| 0 | 25.12 | 25.12 | 25.12 | 25.12 |

TABLE 12

EC 50 values with 95% confidence limits and method of analysis used.

| Treatment Composition | EC50 mL product /hL | 95% confidence limits | | Method of analysis (method selected as one best fitting data) |
|---|---|---|---|---|
| | | low | High | |
| B | 496.6 | 366.1 | 637.0 | Maximum Likelihood-Probit |
| C | 452.6 | 43.3 | 1804.7 | Maximum Likelihood-Angular |
| E | 412.5 | 274.5 | 551.1 | Maximum Likelihood-Probit |
| D | 541.1 | 400.8 | 668.3 | Maximum Likelihood-Probit |
| C/D 1:1 | 565 | N/D | N/D | Maximum Likelihood-Probit |
| C/D 3:1 | 278.3 | 0.1 | 936.7 | Maximum Likelihood-Probit |
| C/D 1:3 | 334.2 | 223.4 | 454.2 | Maximum Likelihood-Probit |
| C/E 1:1 | 148.7 | 94.8 | 214.6 | Maximum Likelihood-Probit |
| C/E 3:1 | 260.8 | 162 | 361.7 | Maximum Likelihood-Probit |
| C/E 1:3 | 365.6 | 267.5 | 466.2 | Maximum Likelihood-Probit |
| D/E 1:1 | 364.9 | 235.7 | 499.6 | Maximum Likelihood-Probit |

TABLE 12-continued

EC 50 values with 95% confidence limits and method of analysis used.

| Treatment Composition | EC50 mL product /hL | 95% confidence limits low | High | Method of analysis (method selected as one best fitting data) |
|---|---|---|---|---|
| D/E 3:1 | 587.1 | 548.6 | 628.2 | Trimmed Spearman-Karber |
| D/E 1:3 | 381.8 | 43.7 | 957.8 | Maximum Likelihood-Probit |

There results demonstrate the efficacy of the compositions of the invention. In addition, a synergistic effect was shown between particularly compositions C (Tagetes oil) and E (Wintergreen oil). A mixture of Tagetes/Wintergreen 1:1 mixture was 2.8 times more active than the Wintergreen alone formulation and three times as active as the Tagetes oil alone formulation.

No phytotoxicity was seen with any formulation at rates up to and including 3000 mL product/hL on bean leaves.

EXAMPLE 5

Synergistic Effects Against Whitefly

Composition B, and its individual constituents, in compositions C, D and E as described above, in varying amounts were tested against whitefly scales. LD 50 values were determined 7 days after application, using methods analogous to those described above in relation to EC 50 values for mites. The method of analysis (method selected as one best fitting data) in this case was the Maximum Likelihood-Probit.

LC 50 values based on three replicates are shown in Table 13.

TABLE 13

| Treatment | LC 50 mL product/hL |
|---|---|
| Composition B | 177.9 |
| Tagetes (C) | 407.6 |
| Wintergreen (E) | 338.1 |
| Thymus (D) | 37.6 |
| Tagetes (C)/Thymus (D) 1:1 | 28.8 |
| Tagetes (C)/Thymus (D) 3:1 | 26.6 |
| Tagetes (C)/Thymus (D) 1:3 | 169.5 |
| Tagetes (C)/Wintergreen (E) 1:1 | 180.9 |
| Tagetes (C)/Wintergreen (E) 3:1 | 376.2 |
| Tagetes (C)/Wintergreen (E) 1:3 | 309.0 |
| Thymus (D)/Wintergreen (E) 1:1 | 14.7 |
| Thymus (D)/Wintergreen (E) 3:1 | 83.1 |
| Thymus (D)/Wintergreen (E) 1:3 | 94.9 |

These results illustrate that, depending upon the relative concentrations, synergy between combinations of Tagetes and Thymus oils, Thymus and Wintergreen oils, and Thymus and Wintergreen oils occur when used against whitefly.

The invention claimed is:

1. A pesticidal composition comprising (i) a mixture of tagetes oil and thyme oil in a ratio of from 3:1 to 1:1, wherein the total amount of such oils does not exceed 10% w/w in the composition; (ii) an agriculturally acceptable carrier oil and (iii) an emulsifier.

2. A pesticidal composition according to claim 1 which further comprises a compound which remediates symptoms of viral infection.

3. A pesticidal composition comprising (i) a mixture of tagetes oil and thyme oil in a ratio of from 3:1 to 1:1; (ii) an agriculturally acceptable carrier oil; (iii) an emulsifier; and (iv) a compound which remediates symptoms of viral infection.

4. A composition according to claim 3 which contains no more than 10% w/w of component (i) in the composition.

5. A composition according to claim 1, which contains no more than 5% w/w of component (i) in the composition.

6. A composition according to claim 5 which contains no more than 1.5% w/w of component (i) in the composition.

7. A composition according to claim 1 wherein component (ii) is selected from canola oil, sunflower oil, cottonseed oil, palm oil and soybean oil.

8. A composition according to any claim 1 wherein the emulsifier is a natural organic emulsifier.

9. A composition according to claim 1 wherein the component (iii) is present in an amount of from 1 to 20% w/w in the composition.

10. A composition according to claim 1 further comprising a compound which remediates symptoms of viral infection.

11. A composition according to claim 10 wherein the said compound is salicylic acid or an ester thereof.

12. A composition according to claim 11 wherein the said compound is methyl salicylate.

13. A composition according to claim 10 wherein the said compound is contained within an essential oil.

14. A composition according to claim 13 wherein the essential oil is wintergreen oil.

15. A formulation for administration to plants, the formulation comprising a composition according to claim 1, and water.

16. A method for killing or controlling insect pests which method comprises applying to the pests or to the locus thereof, a composition according to claim 1.

17. A method according to claim 16 wherein the composition includes a compound which remediates viral symptom infection whereby the treatment provides a combined pesticidal and viral symptom remediation effect.

18. A method according to claim 16, wherein the composition or formulation is administered together with another insecticide or acaricide.

19. A method according to claim 16 wherein the composition is applied to a crop in an amount of less than 5 liters per hectare.

20. A method according to claim 19 wherein the composition is applied to a crop in an amount of about 2 liters per hectare.

21. A method for the combined pesticidal/viral symptom remediation which comprises use of a composition according to claim 1.

22. A method for adjuvantizing an insecticide or acaricide which comprising using said insecticide or acaricide in combination with a composition according to claim 1.

23. A method for controlling insects or arachnids, the method comprising administration of a composition according to claim 1 to crops at a rate of less than 5 liters per hectare.

24. A composition according to claim 10 wherein the said compound is a compound which reduces ethylene production.

* * * * *